United States Patent [19]

Smith

[11] Patent Number: 4,672,967

[45] Date of Patent: Jun. 16, 1987

[54] TAG IMPLANTATION SYSTEM AND METHOD

[76] Inventor: David V. Smith, 14014 Salmon Creek Ave., Vancouver, Wash. 98686

[21] Appl. No.: 853,543

[22] Filed: Apr. 18, 1986

[51] Int. Cl.⁴ ............................................. A61B 17/00
[52] U.S. Cl. ...................................... 128/330; 119/3; 604/57; 604/891
[58] Field of Search ................... 604/57, 891; 128/316, 128/217, 330; 119/3

[56] References Cited

U.S. PATENT DOCUMENTS

| | | | |
|---|---|---|---|
| 2,121,787 | 6/1938 | Dahlgren | 128/330 X |
| 3,313,301 | 4/1967 | Jefferts et al. | 128/330 |
| 3,369,525 | 2/1968 | Debrotnic et al. | 604/891 |
| 3,545,405 | 12/1970 | Jefferts | 128/330 |
| 3,820,545 | 6/1974 | Jefferts | 128/330 |
| 4,233,964 | 11/1980 | Jefferts et al. | 128/330 |

*Primary Examiner*—C. Fred Rosenbaum
*Assistant Examiner*—Ralph Lewis
*Attorney, Agent, or Firm*—Kolisch, Hartwell & Dickinson

[57] ABSTRACT

A system for implanting a magnetizable tag into a macro-organism is provided. The system includes an organism receiving element for receiving an abutted surface of the macro-organism, a mechanism for advancing the tag toward the receiving element, a guide annulus for providing an injection path of travel and a magnet for magnetizing in alignment with the path of travel, and a magnet for magnetizing the tag as it is passed through the guide annulus. In one aspect of the invention, the guide annulus comprises a tubular member having a blunt implantation end for abutment with the macro-organism at the moment of implantation.

19 Claims, 5 Drawing Figures

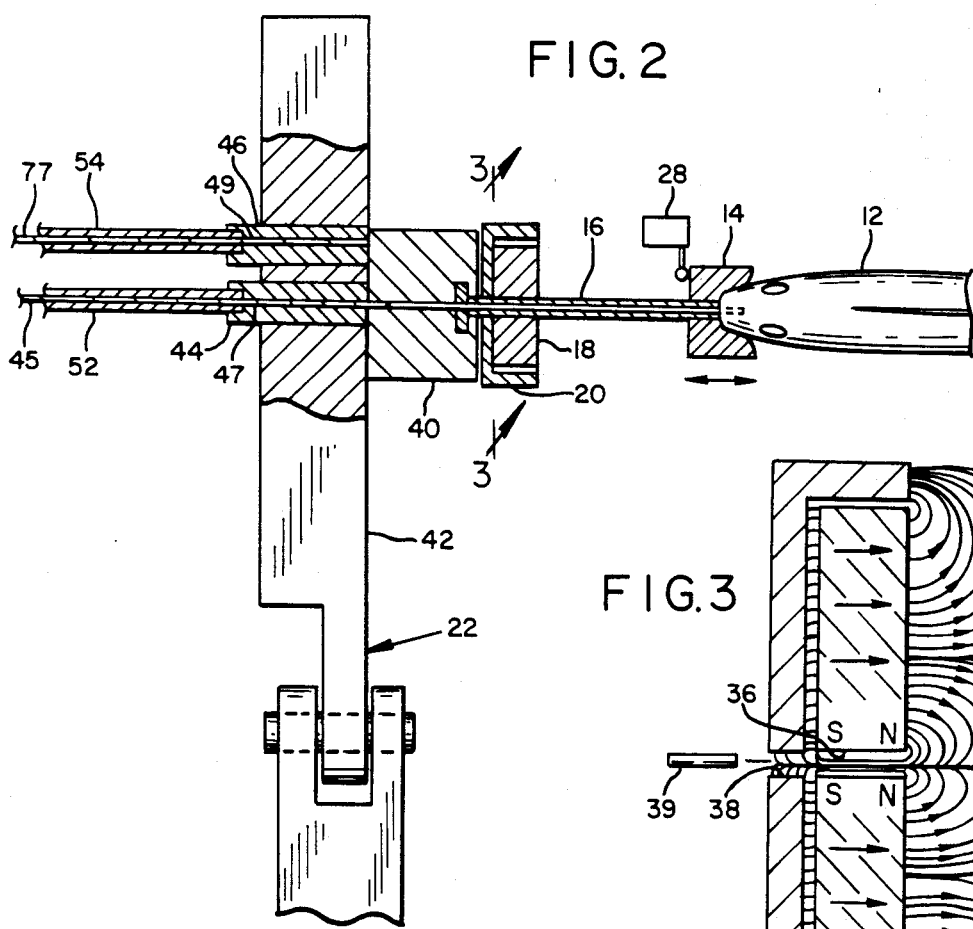
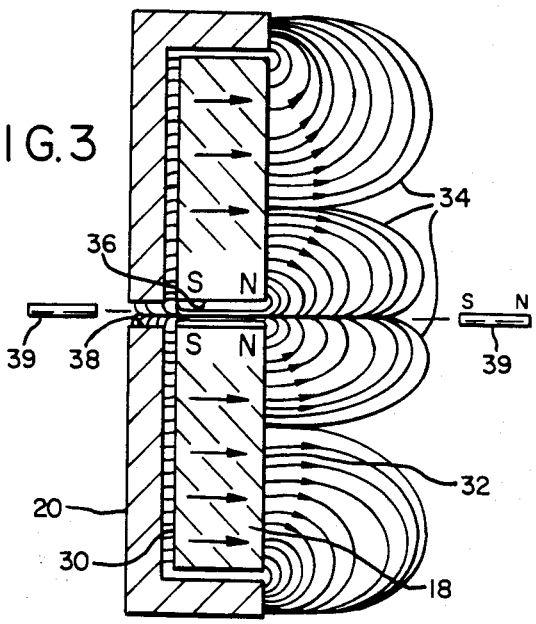
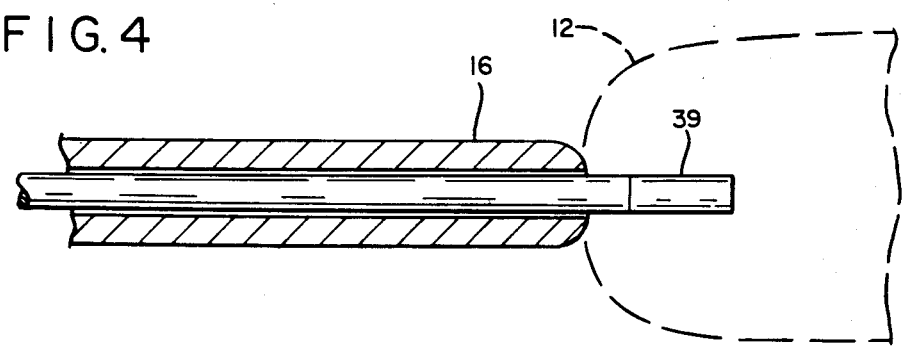
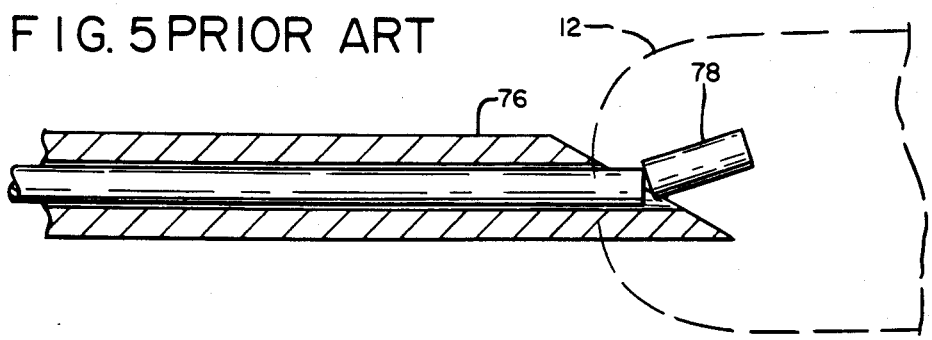

TAG IMPLANTATION SYSTEM AND METHOD

BACKGROUND OF THE INVENTION

This invention relates generally to systems for tagging macro-organisms, and more particularly to an apparatus and method for tagging macro-organisms, such as fish, for subsequent detection and analyses.

For many years, biologists have been attempting to track the migratory patterns of animals. Particular emphasis has been placed upon studying the migratory habits of fish. There are several reasons for this, but perhaps the most important reason is because of the susceptibility of fish to environmental damage and to over-fishing. In recent years, the increasing need for hatcheries to propagate, grow and subsequently release migratory fish, such as salmon, steelhead and striped bass, has lead to a strong emphasis on developing an appropriate method for marking such fish. Because the fish are at the fingerling size when released from hatcheries, there has been a real problem with developing a system for indelibly marking such fish without affecting their swimming ability or their migratory habits.

A system has been developed in which a minute piece of stainless steel wire, commonly called a tag, is inserted into the cartilaginous region of the nose of the fish. The wire tag is typically magnetized so that when the fish return to spawn, biologists can electronically sort out those fish which have been tagged. The tags are indelibly marked so that the time and place of release can be determined. Two such systems are disclosed in U.S. Pat. Nos. 3,820,545 and 3,545,405 to Jefferts.

In a typical tag implantation operation, wire is intermittently advanced, cut and implanted into the cartilaginous region in the nose of the fish. Each fish is then passed through a large magnetic field, which tends to create the desired permanent magnetic charge in the implanted tag. Because the magnet must be large enough to receive the largest tagged fish, it is difficult to present a concentrated magnetic field to the wire tag. Also, because tag placement into the fish is not always coincidence with the linear extension of the fish, it is possible that the tag may not pass through the magnet in a linear disposition, which is the disposition which results in the strongest magnetic field being imparted to the tag. This is because some fish are not tagged in the nose, but rather are tagged in the gill area, where the disposition will be perpendicular to the linear extension of the fish.

It is imperative that a strong magnetic charge be imparted to the tag, because, as mentioned above, it may be as many as six years before the fish returns to spawn. Anything less than a strong magnetic charge might tend to dissipate, thus preventing electronic detection. Because of the inability to always impart a strong charge to the wire tags, extremely sensitive and therefore expensive tag detection equipment must be utilized to prevent any tagged fish from passing through the sensing mechanism without being detected.

Another drawback with conventional tagging systems is that they often result in the fish being impaled by an implantation needle, through which the tag is passed. This impaling process results in severe trauma to the fish, to an extent far greater than would be necessary by insertion of the tag alone. The injection can kill the fish or the injury can affect their migratory habits, which would defeat the purpose of the tagging operation.

It is therefore an object of the present invention to overcome the drawbacks and limitations of the prior art proposals. More specifically, the invention has as its objects:

(1) the provision of means for providing a much stronger magnetic field;

(2) to provide a method of applying a magnetic field to a fish tag in which the alignment of the tag passing through the magnetic process will be linear, rather than lateral, so that the ends of the tag will become the north and south poles, regardless of the ultimate positioning of the tag within the fish or other macro-organism;

(3) the provision of a system for applying a magnetic field to a fish tag which is simple, relatively inexpensive, which may be operated by one with little or no training, and which may be retrofitted into conventional tag implantation equipment;

(4) to provide a system which performs implantation and magnetization of a metallic fish tag in a single operation rather than the time-consuming and troublesome two-step process now being utilized;

(5) to develop a fish tag magnetization system which permits a reduction in the sophistication and therefore the cost of the detection equipment used for quality control and to recover and identify the tagged fish;

(6) the development of a tag magnetization system which is usable with tags having a wide variety of forms and materials; and (7) to provide a tag implantation process which reduces the trauma to the fish being tagged.

SUMMARY OF THE INVENTION

The above objects are best achieved by providing a system for implanting a magnetizable tag and for magnetizing the tag as it passes through a guide annulus which normally is in the form of a tubular member. With such a magnetization system, the magnetic field is concentrated on the tag, and does not require that the entire organism be passed through a much larger, and therefore less concentrated, magnetic field. The tubular member may include a blunt implantation end which is abutted with the organism at the moment of implantation. With the use of such an implantation end, trauma to the organism is reduced.

The means for providing magnetization normally includes a toroid-shaped magnetization member which encompasses the guide annulus. A soft iron shield may be provided adjacent the magnetization member to concentrate the magnetic flux into a most concentrated field pattern.

Tag supply means for advancing a tag supply toward the organism is also normally included. This tag supply means is typically offset with respect to the means for advancing the tag toward the organism. In such embodiment, cutter means is provided for cutting off a tag from the tag supply means, and then transversely shifting the cut tag into alignment with the means for advancing the tag toward the organism. It is also normal that the tag advancement means is independent of the tag supply means.

Another aspect of the invention comprises a method for implanting a magnetizable tag which comprises the steps of (1) positioning the organism to be tagged in abutment with an organism receiving element, (2) magnetizing the tag by advancing it toward the organism and through a substantially toroid-shaped magnet, and (3) injecting the tag by passing the tag through a tubular member and into the organism.

These and other features and advantages of the present invention will become more apparent as this description continues.

BRIEF DESCRIPTION OF THE DRAWINGS

FIG. 2 is an enlarged, fragmentary, schematic view corresponding to that of FIG. 1 except that the cutter is shown to be in an extended position immediately prior to cutting of the tag from the supply of wire, so that the tag is still in alignment with the wire supply guide tube;

FIG. 3 is an enlarged, schematic, sectional plan view taken along line 3—3 of FIG. 2, showing the toroid magnetic and its pole shade;

FIG. 4 is a schematic view depicting the blunt implantation needle as implantation is taking place; and FIG. 5 is a schematic view of a prior art, sharpened needle as implantation is taking place.

DETAILED DESCRIPTION OF THE PREFERRED EMBODIMENT

Figure 1:
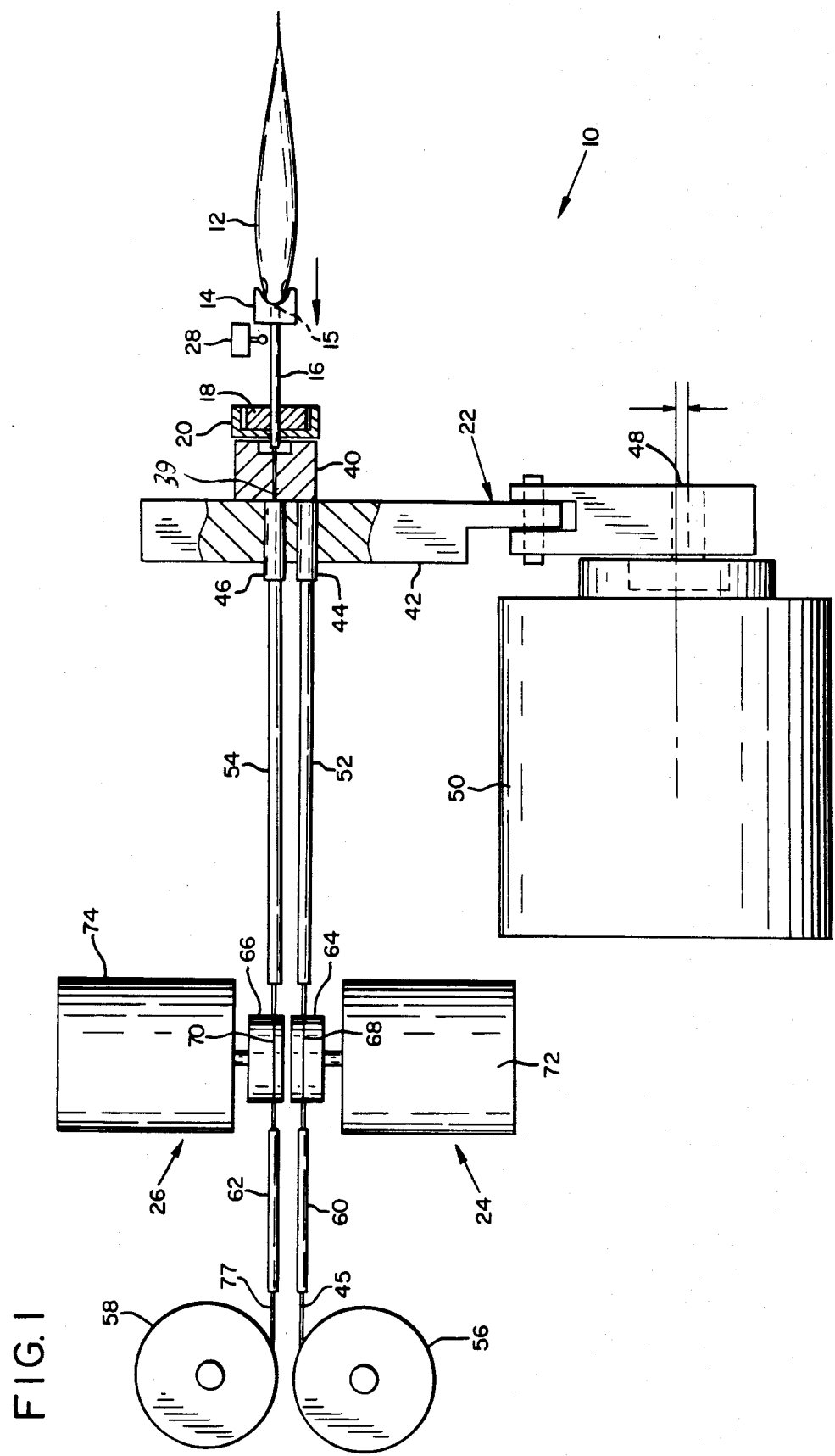
FIG. 1 is a schematic plan view of a first embodiment of the present invention showing the tag cutter in a retracted position with the cut tag being positioned in alignment with the injection needle.

One preferred form which the invention may take has been depicted in FIGS. 1 through 5. Referring first to FIG. 1, the system for implanting a magnetizable tag has been generally indicated with the numeral 10. The system is shown to be implanting a tag into a fish 12, although system 10 may be used to tag other macroorganisms as well. The system generally includes a head mold 14, an implantation needle 16, a magnet 18 having a soft iron shade 20 to concentrate the magnetic field, a cutter mechanism 22, means 24 for advancing a tag supply toward the cutter mechanism 22, and means 26 for advancing the cut tag. The depicted system 10 has been designed to utilize wire as a tag material. Specifically, 300 series stainless steel wire has typically been utilized with this system. Normally, stainless steel is not magnetic, but through the cold drawing process of wire sizing, the material "work hardens," which changes its molecular structure to facilitate the retention of magnetization once the wire has passed through a strong magnetic field. However, it should be appreciated that the invention is not limited to use with wire tag material. There may be other materials such as metallic plate and the like which may be implanted into the fish through use of the present invention. The use of such plate or other tag forms is possible by merely modifying the feed and cutter apparatus.

The components of system 10 will now be discussed in more detail, beginning with head mold 14. This head mold is of conventional design and is typically formed to complement the shape and size of a fish which is being tagged. Head mold 14 includes a central aperture 15 through which implantation needle 16 extends. Implantation needle 16 is formed of metallic but magnetically permeable material so that magnetization of the tag can be effected through the needle wall. The position of the needle with respect to head mold 14 is such that when a fish 12 is placed in position in the head mold, the needle comes into direct abutment with the cartilaginous region of the nose of the fish. This portion of implantation needle 16 is shown best in FIG. 4, and will be discussed in more detail later in this description.

Head mold 14 and implantation needle 16 are spring-biased outwardly toward fish 12 so that the head mold and the needle can be pushed inwardly when tag implantation is desired. Means is provided for automatically activating the means 26 for advancing a cut tag once this inward displacement has taken place. This automatic activation means might include a photo cell, but in the depicted embodiment a micro switch 28 has been shown. It is also possible that the activation be manual by a push button or a foot switch, but this embodiment is not the preferred mode so has not been depicted.

FIG. 3 depicts magnet 18 as being substantially toroid or doughnut-shaped, and includes an upstream face 30 and a downstream face 32. In the depicted embodiment, the south pole of the magnet is the upstream face and the north pole is the downstream face. A soft iron shade 20 is shaped to cover all but the downstream face 32 of magnet 18. As shown by the schematic magnetic field lines 34 in FIG. 3, shade 20 serves to concentrate the field in the central opening 36 which extends through toroid-shaped magnet 18. A corresponding aperture 38 extends through shade 20 so that the tag 39 to be magnetized can be passed through the magnet assembly. While shade 20 is not an essential part of the invention, without this feature, the field would be more dispersed about the magnet and thereby result in a less intense field being applied to the tag. However, even without shade 20, system 10 provides for far more intense magnetization than is possible in prior art systems which typically pass the entire fish through a magnetic field.

Although a toroid-shaped magnet has been depicted in FIG. 3, it is possible that other types of magnets be used in magnetizing the tag. Specifically, two or more aligned bar magnets (not shown) may be utilized, or a helically coiled electromagnet may be employed. However, these alternate forms do not appear to be as effective as the toroid-shaped magnet of the depicted embodiment.

As shown in FIGS. 1 and 2, implantation needle 16 extends entirely through the central opening 36 in magnet 18 and the aperture 38 in shade 20, and into a needle holder 40 which is disposed behind the magnet and shade. Needle holder 40, needle 16 and the magnet and shade are fixed with respect to each other. Needle holder 40 is typically formed of carbide or other hard metal because it cooperates with cutter mechanism 22 to cut the wire tags, as will now be described.

Cutter mechanism 22 is depicted best in FIG. 2. The mechanism includes a cutter bar 42 with a pair of carbide cutters 44 and 46. Cutter 44 is designed to cut the wire tag material 45 as it advances toward the fish, while cutter 46 is capable of, when necessary, cutting the pushing wire 77 which is provided as part of the means 26 for advancing the cut tag. In the normal operation of the system, the leading end of push wire 77 is clipped off only when it is first activated for a series of cutting operations. By clipping off the leading end of push wire 77, the position of the clipped end can be precisely determined. Each of the cutters includes a centrally disposed channel 47 and 49, as shown in FIG. 2. The diameter of channels 47 and 49 is normally approximately 0.012 inch, or only slightly more than the 0.010 inch diameter of the wire tag material being utilized. The driving motion for cutter bar 42 is provided by an eccentric cam 48 which is driven by a cutter drive motor 50.

The spacing between the channels 47 and 49 of carbide cutters 44 and 46 corresponds to distance between a pair of flexible guide tubes 52 and 54. As will be described more fully below, flexible guide tube 52 conveys wire tag supply 45 to cutter mechanism 22, while flexible guide tube 54 holds the push wire supply 77 for pushing the cut tag from the cutter mechanism 22, through implantation needle 16, and into the fish.

The means 24 for advancing the tag supply 45, and the means 26 for advancing the cut tag will now be described in more detail. A wire tag supply reel 56 is provided to store and supply wire which is subsequently cut and implanted as tags. A push wire supply reel 58 is also provided for supplying push wire. Because the type and size of wire is usually identical for these two parts of system 10, the reels 56 and 58 are also normally of the same design. A wire tag supply infeed guide tube 60 and a push wire infeed guide tube 62 are provided which guide the wire supplies to a pair of coaxially mounted but relatively rotatable drive wheels 64 and 66. Each of the drive wheels 64 and 66 normally includes a central groove 68, 70 which, in cooperation with a resilient platen (not shown), provides sufficient surface contact and friction to cause the wires to be grasped and engaged by drive wheels 64 and 66. A tag wire feed motor 72 and an injection motor 74 are mounted to provide power to drive wheels 64 and 66, respectively. These motors are conventional, reversible stepper-type motors which, upon the appropriate control signal, advance either the wire tag supply 45 or the push wire supply 77 toward cutter mechanism 22. Because relative rotation is permitted between drive wheels 64 and 66, it is not necessary that the wires be advanced at the same time. In fact, in normal operation, they will be advanced at different times. Also during normal operation, tag wire feed motor 72 will be reversing at regular intervals to retract the push wire.

In order to further understand the advantages of the present invention, reference should now be made to FIGS. 4 and 5. FIG. 4 depicts the blunt implantation needle 16 of the present invention, while FIG. 5 depicts a conventional sharp needle. In conventional tag implantation operations, a sharp needle such as that shown at 76 in FIG. 5 is impaled into the fish as a first step of the operation. A wire tag 78 is then pushed through the needle and into the cartilaginous region of the nose of the fish. Because the outer diameter of needle 76 must be substantially larger than the outer diameter of tag 78, the resulting hole in the fish is much larger than the tag size requires. This causes unnecessary trauma to the fish, which can prove fatal to a significant percentage of the tagged population. Also, when the sharpened needle 76 is withdrawn, there is some possibility that tag 78 may be dislodged with it. Another drawback is that because of the angled design of the sharp needle 76, tag 78 may have a tendency to be pushed upwardly as it is displace into the fish. This tendency is depicted in FIG. 5. The drawback with this is that it may result in the tag being lodged in something other than a perfectly linear disposition. With prior art tag magnetization operations, this was a serious drawback because nonlinear disposition within the nose of the fish would reduce the effectiveness of the magnetic field being applied to the tag. The most ideal disposition of a tag is end-to-end as it passes through the magnetic field. As mentioned above, in prior art tagging operations, the tag is magnetized by passing the entire fish through the magnetic field. If the tag is not disposed in a linear position along the fish, then the most effective magnetization pattern will not be applied. It also would make a subsequent detection of the tag more difficult.

With the blunt implantation needle 16 of the depicted embodiment (shown in FIG. 4), the needle itself is not designed to penetrate the nose of a fish. Rather, the blunt end of the needle merely abuts the nose of the fish, and only the tag 39 is inserted into the fish. This result in far less trauma to the fish, expedites healing of the implantation wound and reduces the likelihood that the tag will become skewed or lodged in the fish in something other than a linear disposition. Thus, while the blunt needle of the depicted embodiment is not an essential part of the invention, its advantages are manifest.

Operation of the Depicted Embodiment

While it is believed that the above discussion will make the operation of the depicted embodiment clear, a brief discussion of that operation will follow. Making reference to FIG. 1, to initiate a tagging operation, the head of fish 12 is placed into the head mold 14 so that the blunt end of implantation needle 16 abuts the nose of the fish. The fish is then pushed forwardly, causing micro switch 28 to activate injection motor 74. This activates injection motor 74 and causes it to rotationally advance, so that drive wheel 66 engages and advances push wire 77 toward the fish. The push wire 77 thus pushes the previously cut tag 39 through needle holder 40, magnet shade 20 and magnet 18, implantation needle 16, into the nose of the fish as shown in FIG. 4. As the tag 39 passes through toroid magnet 18, a strong magnetic field is imparted to the tag, establishing a north and south pole as indicated in FIG. 3. As described above, the concentration of this field is magnified due to the presence of shade 20. As shown in FIG. 4, this implantation technique will result in implantation of tag 39 in a linear disposition in fish 12, while causing minimum trauma because the hole in the nose of the fish is no greater in diameter than the size of the implanted tag.

When tagging is complete, the fish is withdrawn, and head mold 14 retracts to the position indicated in FIG. 1. At this time, tag wire feed motor 72 reverses to retract the push wire so that it is not cut off in subsequent shifting of the cutter bar. Retraction of head mold 14 causes micro switch 28 to activate cutter drive motor 50 to step the motor to a position such that eccentric 48 causes cutter bar 42 to be extended in the position depicted in FIG. 2. Because guide tubes 52 and 54 are flexible, this relative movement between the downstream and upstream ends of the guide tubes is possible. When cutter bar 42 has been positioned as depicted in FIG. 2, tag wire motor 72 is activated to rotationally advance the wire tag supply until the forward or downstream end of that supply extends slightly into needle holder 40, again as shown in FIG. 2. Cutter drive motor 50 then rotates eccentric 48 by 180°, causing cutter bar 42 to retract to the position depicted in FIG. 1. This retraction causes the wire supply 45 to be cut, leaving tag 39 positioned in the upstream end of needle holder 40. At this point, the system is ready for reactivation and injection of this next tag into the next fish.

While a preferred embodiment of the present invention has been above-described, it should be understood that various modifications and changes in the depicted embodiment may be possible by those with ordinary skill in the art. Such modifications and changes should be considered within the scope of the present invention and are encompassed by the following claims.

It is claimed and desired to secure by Letters patent:
1. A system for implanting a magnetizable tag into a macro-organism comprising:

an organism receiving element for receiving an abutted surface of the macro-organism to be tagged;

means for advancing the tag toward said receiving element, said advancing means being interconnected with said receiving element;

guide annulus means associated with said advancing means for providing an injection path of travel; and magnetization means for magnetizing the tag as the tag is passed through said guide annulus.

2. The system of claim 1, wherein said guide annulus is defined by a tubular member.

3. The system of claim 2 wherein said tubular member includes blunt implantation end means for non-penetrating abutment with the macro-organism at the moment of implantation.

4. The system of claim 1, wherein said magnetization means comprises a magnet system which substantially surrounds said guide annulus.

5. The system of claim 1, wherein said magnetization means comprises a toroid magnetization member surrounding said guide annulus.

6. The system of claim 5, wherein said magnetization member includes upstream and downstream faces which extend substantially normal to injection path of travel, with one of the faces comprising a north pole and the other a south pole.

7. The system of claim 2, wherein said magnetization means comprises a toroid magnetization member in concentric disposition with said tubular member.

8. The system of claim 6, further comprising a soft iron shield defining a central aperture in alignment with a central opening defined by said magnetization member, said shield substantially covering said upstream face of said magnetization member.

9. The system of claim 8, wherein said shield substantially covers all but said downstream face of said magnetization member.

10. The system of claim 1, further comprising tag supply means for advancing a tag supply generally toward said organism receiving element along a supply path of travel which is substantially parallel to said injection path of travel.

11. The system of claim 10, wherein said injection and supply paths of travel are offset with respect to each other.

12. The system of claim 11, further comprising cutter means for cutting off a tag from said tag supply means, said cutter means being reciprocal between one position in alignment with said supply path of travel and a second position in alignment with said injection path of travel, said cutter means further comprising means for conveying a cut tag from said supply path of travel to said injection path of travel.

13. The system of claim 10, wherein said tag advancement means comprises means for pushing the tags in a downstream direction, and wherein said tag advancement means is independent of said tag supply means.

14. The system of claim 13, wherein said tag supply means provides a supply of wire, and said means for pushing the tags comprises a push wire.

15. The system of claim 14, wherein said tag supply means and said means for pushing the tags each includes drive means which engages and drives the wire supply and said push wire.

16. A method for implanting a magnetizable tag into a macro-organism comprising:

positioning the organism to be tagged in abutment with an organism receiving element;

magnetizing the tag to be implanted by advancing the tag generally toward the organism and through a substantially toroid-shaped magnet having north and south poles; and injecting the magnetized tag by passing the tag through a tubular member and into the organism.

17. The method of claim 16, further comprising first concentrating the magnetic field of the magnet by positioning a soft iron shield against one of the poles of the magnet.

18. The method of claim 16, wherein said step of injecting the tag comprises positioning a blunt implantation member in abutment with the organism, and then, while maintaining the implantation member in a non-penetrating abutment with the organism, injecting the tag through the implantation member and into the organism.

19. A method for implanting a magnetizable tag into a macro-organism comprising:

positioning the organism to be tagged in abutment with an organism receiving element;

magnetizing the tag to be implanted by advancing the tag generally toward the organism and through a tubular member with a surrounding magnetic field; and injecting the magnetized tag by passing the tag out of the tubular member and into the organism.

* * * * *